(12) United States Patent
Greene (10) Patent No.: US 7,498,163 B2
(45) Date of Patent: Mar. 3, 2009

(54) PROCESS FOR REDUCING SOLID WASTE VOLUME AND LANDFILL MASS

(75) Inventor: Annel K. Greene, Clemson, SC (US)

(73) Assignee: Clemson University, Clemson, SC (US)

( * ) Notice: Subject to any disclaimer, the term of this patent is extended or adjusted under 35 U.S.C. 154(b) by 452 days.

(21) Appl. No.: 11/005,815

(22) Filed: Dec. 7, 2004

(65) Prior Publication Data

US 2005/0141966 A1 Jun. 30, 2005

Related U.S. Application Data

(63) Continuation of application No. 09/983,012, filed on Oct. 18, 2001, now Pat. No. 6,835,560.

(51) Int. Cl.
C02F 3/00 (2006.01)
C02F 3/34 (2006.01)
B09B 3/00 (2006.01)

(52) U.S. Cl. ............ 435/262; 435/42; 405/129.15; 405/129.25; 405/129.27; 405/129.65; 405/129.95

(58) Field of Classification Search ............ 435/262, 435/262.5; 405/129.15, 129.25, 129.27, 405/129.65, 129.95
See application file for complete search history.

(56) References Cited

U.S. PATENT DOCUMENTS

| | | | |
|---|---|---|---|
| 2,178,818 A | 11/1939 | Earp-Thomas | |
| 2,209,613 A | 7/1940 | Roeder | |
| RE22,444 E | 2/1944 | Shook | |
| 2,477,815 A | 8/1949 | Mallory | |
| 3,232,434 A | 2/1966 | Albersmeyer | |
| 3,459,303 A | 8/1969 | Bradley | |
| 3,485,750 A | 12/1969 | Albertson | |
| 3,577,341 A | 5/1971 | Keith, Jr. et al. | |
| 3,591,491 A | 7/1971 | Smith et al. | |
| 3,607,737 A | 9/1971 | Gamer | |
| 3,617,537 A | 11/1971 | Vermette | |
| 3,638,793 A | 2/1972 | Peck | |
| 3,660,277 A | 5/1972 | McWhirter et al. | |
| 3,709,364 A | 1/1973 | Savage | |
| 3,803,029 A | 4/1974 | Blecharczyk | |
| 3,806,448 A | 4/1974 | Smith et al. | |
| 3,825,494 A | 7/1974 | Call et al. | |
| 3,838,199 A | 9/1974 | Coe et al. | |
| 3,846,292 A | 11/1974 | Lecompte, Jr. et al. | |
| 3,918,404 A | 11/1975 | Bunger | |
| 3,982,499 A | 9/1976 | Frankl | |
| 3,996,105 A | 12/1976 | Harrison et al. | |
| 4,003,790 A | 1/1977 | Barnes et al. | |
| 4,042,458 A | 8/1977 | Harrison et al. | |
| 4,132,637 A | 1/1979 | Key et al. | |
| 4,178,239 A | 12/1979 | Lowther | |
| 4,214,887 A | 7/1980 | van Gelder | |
| 4,256,574 A | 3/1981 | Bhargava | |
| 4,404,110 A | 9/1983 | Beazley et al. | |
| 4,451,567 A | 5/1984 | Ishibashi et al. | |
| 4,608,338 A | 8/1986 | Hsieh | |
| 4,752,316 A | 6/1988 | Plovanich et al. | |
| 4,915,842 A | 4/1990 | Kearney et al. | |
| 5,011,599 A | 4/1991 | Kearney et al. | |
| 5,070,016 A | 12/1991 | Hallberg | |
| 5,078,965 A | 1/1992 | Pearson | |
| 5,342,522 A | 8/1994 | Marsman et al. | |
| 5,424,195 A | 6/1995 | Volkwein | |
| 5,447,850 A | 9/1995 | McCann | |
| 5,466,367 A | * 11/1995 | Coate et al. | ............ 210/96.1 |
| 5,520,888 A | 5/1996 | Berndt | |
| 5,633,163 A | * 5/1997 | Cameron | ............ 435/262 |
| 5,641,679 A | * 6/1997 | Pierce | ............ 435/262 |
| 5,679,257 A | * 10/1997 | Coate et al. | ............ 210/695 |
| 5,688,685 A | * 11/1997 | Pierce | ............ 435/262 |
| 5,707,856 A | 1/1998 | Higa | |
| 5,753,494 A | 5/1998 | Hater et al. | |
| 5,773,283 A | * 6/1998 | Pierce | ............ 435/262 |
| 5,854,061 A | * 12/1998 | Horn et al. | ............ 435/262.5 |

(Continued)

FOREIGN PATENT DOCUMENTS

JP 1998 10225694 8/1998

(Continued)

OTHER PUBLICATIONS

Finch, et al., Recovery of a Marker Strain of *Escherichia coli* from Ozonated Water by Membrane Filtration, p. 2894-2896, Dec. 1987, Applied and Environmental Microbiology.

(Continued)

*Primary Examiner*—Herbert J. Lilling
(74) *Attorney, Agent, or Firm*—Dority & Manning, P.A.

(57) ABSTRACT

The present invention is related to a process for reducing solid waste volume and landfill mass. More particularly, the process of the present invention is directed to reducing organic waste with or without production and collection of a useful product. The process of the present invention involves supplying at least one oxidizing agent in the presence of an aqueous medium into organic materials. The oxidizing agent oxidizes and breaks down a portion of these materials. After addition of the oxidizing agent, at least one species of microorganism may be supplied into the channel and the microorganism consumes the oxidized organic material.

10 Claims, 10 Drawing Sheets

U.S. PATENT DOCUMENTS

| | | | |
|---|---|---|---|
| 5,897,785 | A | 4/1999 | Billings |
| 6,056,885 | A | 5/2000 | Wasinger |
| 6,077,548 | A | 6/2000 | Lasseur et al. |
| 6,117,324 | A | 9/2000 | Greene et al. |
| 6,303,034 | B1 * | 10/2001 | Kamiya et al. ............. 210/603 |
| 6,340,581 | B1 | 1/2002 | Gaddy |
| 6,423,229 | B1 | 7/2002 | Mao |
| 6,500,333 | B1 | 12/2002 | Greene |
| 6,835,560 | B2 * | 12/2004 | Greene ....................... 435/167 |
| 2002/0061270 | A1 | 5/2002 | Osborne |
| 2002/0192774 | A1 | 12/2002 | Ahring et al. |

FOREIGN PATENT DOCUMENTS

| | | |
|---|---|---|
| JP | 2000 189103 | 7/2000 |
| JP | 2001 025789 | 1/2001 |

OTHER PUBLICATIONS

Restaino, et al., Efficacy of Ozonated Water against Various Food-Related Microorganisms, p. 3471-3475, Sep. 1995, Applied and Environmental Microbiology.

Y.H. Chang and B.W. Sheldon, Application of Ozone with Physical Wastewater Treatments to Recondition Poultry Process Waters, p. 1078-1087, Jun. 6, 1988, Journal Series of the North Carolina Agriculture Research Series, Raleigh, NC 27695-7601.

Finch, et al., Comparison of *Giardia lamblia* and *Giardia muris* Cyst Inactivation by Ozone, p. 3674-3680, Nov. 1993, Applied and Environmental Microbiology.

Finch, et al., Ozone Inactivation of *Cryptosporidium parvum* in Demand-Free Phosphate Buffer Determined by In Vitro Excystation and Animal Infectivity, p. 4203-4210, Dec. 1993, Applied and Environmental Microbiology.

B.A. Meiners, R.E. Peters and J.B. Mudd, Effects of Ozone on Indole Compounds and Rat Lung Monoamine Oxidase, p. 99-112, 1977, Environmental Research.

Duane L. Peavy and Edward J. Fairchild II, Toxicologic Interactions between Ozone and Bacterial Exdotoxin, p. 63-71, 1987, Environmental Research.

I.Arana, P.Santorum, A.Muela and I.Barcina, Chlorination and ozonation of waste-water:comparative analysis of efficacy through the effect on *Escherichia coli* membranes, p. 883-888, 1999, Journal of Applied Microbiology.

E. Smet & H. Van Langenhove, Abatement of volatile organic sulfur compounds in odorous emissions from bio-industry, Biodegration 9:273-284,1998.

William A. Feder, Bioassaying for Ozone With Pollen Systems, vol. 37:117-123, Jan. 1981, Environmental Health Prospectives.

Serge Chiron, Antonio Rodriguez and Amadeo Fernandez-Alba, Application of gas and liquid chromatography-mass spectrometry to the evaluation of pirimiphos methyl degradation products in industrial water under ozone treatment, Journal of Chromatography A, 823:97-107, 1998.

I.R. Komanapalli and B.H.S. Lau, Inactivation of bacteriophage λ, *Escherichia coli*, and *Candida albicans* by ozone, Appl Microbiol Biotechnol, 49:766-769, 1998.

Muela, et al., Discharge of disinfected wastewater in recipient aquatic systems: fate of allochthonous bacterial and autochthonous protozoa populations, Journal of Applied Microbiology, 85:263-270, 1998.

Byun, et al., Gamma Irradiation and Ozone Treatment for Inactivation of *Escherichia coli* O157:H7 in Culture Media, Journal of Food Protection, 61:728-730, 1998.

McKenzie, et al., Aflatoxicosis in Turkey Poults is Prevented by Treatment of Naturally Contaminated Corn with Ozone Generated by Electrolysis, Environment and Health, 1094-1102, 1998.

Klare, et al., Degradation of Nitrogen Containing Organic Compounds by Combined Photocatalysis and Ozonation, Chemosphere, 38:2013-2027, 1999.

Yu, et al., Pretreatment and Biodegradability Enhancement of DSD Acid Manufacturing Wastewater, Chemosphere, 37:487-494, 1998.

Watkins, et al., Ozonation of Swine Manure Wastes to Control Odors And Reduce the Concentrations of Pathogens And Toxic Fermentation Metabolites, Ozone Science & Engineering, 19:425-437, 1997.

Evan, III., Environmental Protection Agency, Cincinnati, Ohio, editor: Ozone In Water And Wastewater Treatment, Ann Arbor Science Publishers, Inc., Ann Arbor, Michigan; Copyright 1972.

* cited by examiner

PROCESS FOR REDUCING SOLID WASTE VOLUME AND LANDFILL MASS

RELATED APPLICATIONS

The present application is a Continuation Application of U.S. patent application Ser. No. 09/983,012 filed on Oct. 18, 2001 now U.S. Pat. No. 6,835,560.

BACKGROUND OF THE INVENTION

Virtually all types of human activities generate various types of waste or by-product materials. Many of these materials can be processed to yield substrates that are or may be readily converted into a useful product. Such conversion is desirable for at least three interrelated reasons. First, conversion reduces the load of material that ultimately must be disposed of via traditional waste management methods; second, conversion saves natural resources by more fully utilizing raw products; and third, conversion not only may save energy but may in fact contribute to the supply of energy yielding materials.

Waste has varied forms and characteristics. In terms of the regulation of waste disposal pursuant to federal statutes, rules and regulations, many waste materials are characterized as municipal solid waste pursuant to 42 USC 691 et seq. Other categories of waste materials include animal waste either as it exists in confined animal production facilities or as it may be found in confinement ponds or lagoons. Other wastes from specific industries that may, but are not necessarily included as municipal solid waste, include materials produced during food processing and rendering, wood and timber processing, and chemical and petroleum manufacturing and processing.

Municipal solid waste, more commonly known as trash or garbage, consists of everyday items such as paper, food scraps and yard trimmings that are disposed of and may ultimately end up at landfills. According to the United States Environmental Protection Agency, in 2001 U.S. residents, businesses, and institutions produced more than 229 million tons of municipal solid waste, which amounts to approximately 4.4 pounds of waste per person per day, up from 2.7 pounds per person per day in 1960. Although source reduction, reuse, recycling, and composting can divert portions of municipal solid waste from disposal, a large amount of waste must still be placed in landfills.

Modern landfills are expensive facilities that require a great deal of funding to build and maintain. Landfills must be built in suitable geological areas away from faults, wetlands, flood plains, or other restricted areas. Typically, liners formed from geomembrane or plastic sheets reinforced with two feet of clay on the bottom and sides of landfills must be installed. In addition, general maintenance including insect and rodent control and ground water monitoring add to landfill costs. Also, closure and postclosure care which includes covering landfills and providing long-term care of closed landfills can further add to costs.

A need currently exists for an improved process for reducing solid waste volume and landfill mass. In particular, a need exists for a process that can reduce the volume of municipal solid waste.

SUMMARY OF THE INVENTION

In general, in one embodiment, the present invention is directed to a process and system for producing useable products from organic materials, such as waste materials. For example, in one embodiment, the process of the present invention is directed to producing ethanol from organic waste materials. In this example, the process includes the steps of first collecting waste materials from various sources. The organic waste materials may include lignocellulosic materials, proteinaceous materials, carbohydrate materials, chitin waste materials, household garbage, restaurant waste, agricultural and forestry waste, petroleum or chemical manufacturing waste, or waste water. Any organic-bearing compound that can be oxidized may be used as a starting material. Waste materials can be pre-separated into organic and inorganic materials. If necessary, the waste materials can first be reduced into a smaller size by any of a variety of means such as shredding or grinding. Further, water may also be added to form a mixture that can be subsequently treated. In this mixture, organic materials exist in suspension and/or in true solution.

Once the mixture or solution containing the organic waste materials is prepared, the mixture/solution is contacted with an oxidizing agent such as ozone. Other oxidizing agents may also be used including hydrogen peroxide. Such oxidizing agents may be used either alone or in combination with ozone. The ozone is present in an amount sufficient to convert at least a portion of the organic waste materials into a medium capable of being converted further by an organism, such as being converted into a fermentable medium. For most applications, the ozone should be fed to the aqueous solution at a concentration of at least 0.01 ppm. Desirably, for most applications, the ozone is fed at a concentration close to saturation. In order to increase the amount of ozone that is dissolved into the mixture/solution, the mixture/solution can be cooled, if desired. The mixture/solution may be warmed to increase the rate of degradation of ozone to molecular oxygen and free radical oxygen.

During ozonation, the organic waste materials are oxidized and degraded into less recalcitrant materials. Complex carbohydrates such as cellulose are oxidized into a mixture of smaller molecules including sugars. Before, during or after ozonation, a base, such as a metal hydroxide, or an acid, can be added to the mixture to adjust the pH of the solution. By the ozonation process, the mixture is converted into a medium that is capable of sustaining biological metabolic processes.

After ozonation, the medium can be separated from any undissolved solids. Next, the medium is contacted with organisms which are capable of using the medium to produce a product. In one embodiment, microorganisms are contacted with the medium which causes the medium to undergo fermentation. For instance, microorganisms can be selected so as to produce ethanol from the fermentable substrate. The ethanol can then be collected and used as desired. Ethanol is known to be an effective energy source.

In order to collect the ethanol, the ethanol can be separated from the remainder of the aqueous solution. For instance, the solution produced after fermentation can undergo a distillation process for isolating the ethanol. One skilled in the art will recognize that there are many other ways of collecting products including centrifugation, temperature fractionalization, chromatographic methods and electrophoretic methods. Some products may be gaseous and can be collected by typical gas collection methods.

In another embodiment of the present invention, instead of being converted into ethanol, the oxidized waste materials can be converted into a hydrocarbon gas, such as methane. For example, a genus of methane-producing bacteria is *Methanobacterium*. In this embodiment, the converted medium can be fed directly to the methane-producing organism or, alternatively, the medium can first be converted into ethanol or acetic acid and then fed to the methane-producing organism. Once produced, the methane can be collected in various ways and used as desired.

It should be understood, however, that the process of the present invention can be used to produce other useful products through bioconversion in addition to alcohols and hydrocarbon gases. For example, the products produced by bioconversion of the substrate can be altered by varying the organisms used in the system. The organisms contacted with the mixture can be carefully selected in order to optimize process conditions. The organisms can be, for instance, bacteria, yeast, fungi, algae, genetically engineered microorganisms, or tissue culture. Both prokaryotic and eukaryotic organisms or mixtures thereof can be cultured in the ozonated substrate. The product may be intracellular or extracellular in nature. The product may be particulate, liquid or gaseous. The product may be miscible or immiscible in water. Other products that can be formed according to the present invention include other alcohols, aldehydes, ketones, organic acids, purines, pyrimidines, alkanes, alkenes, alkynes, ethers, esters, amines, proteins, amides, cyclic and aromatic compounds, enzymes, pigments, lipids, phospholipids, peroxides, gums, pharmaceuticals such as vitamins, microbial cellulose and other polymers.

Any of the oxidized and converted organic materials that are not used in the process can be fed to a plant system (including multicellular and unicellular plant systems) and used for irrigation and/or as a food source. The plant system also can remove inorganic and/or heavy metal substances. If necessary, prior to being fed to the plant system, the aqueous solution containing the converted organic materials can be reozonated.

In another embodiment, the process of the present invention is directed to reducing organic waste with or without production and collection of a useful product. In this embodiment, the process involves creating at least one channel in a landfill mass at a landfill site and supplying at least one oxidizing agent in the presence of an aqueous medium into the channel. The landfill mass contains organic materials and the oxidizing agent oxidizes and breaks down a portion of these materials.

In certain embodiments, after addition of the oxidizing agent, at least one species of microorganism may be supplied into the channel and the microorganism consumes the oxidized carbonaceous matter. In some embodiments, suitable oxidizing agents may include ozone and hydrogen peroxide. In certain embodiments, a plurality of channels may be created, each channel being sequentially supplied with an oxidizing agent. In some embodiments, each channel may be supplied with a microorganism. In other embodiments, additional oxidizing agent and additional microorganism may be supplied into each channel to further reduce the landfill mass. In some embodiments, the aqueous medium may comprise water while in other embodiments, the water may be contacted with the oxidizing agent by flowing through a venturi and feeding the oxidizing agent through the venturi. In certain embodiments, the oxidizing agent may be combined with the aqueous solution in a channel and at a concentration of 0.01 ppm.

Channels may have different widths and depths depending on the landfill mass. A channel may have a diameter of at least 0.5 inch. In other embodiments, a channel may have a depth of at least 1 foot. In certain embodiments, a plurality of channels may be positioned at least 6 inches apart from one another. In some embodiments, a plurality of channels may be positioned less than 20 feet apart from one another. In some embodiments, the landfill mass which is contacted with the oxidizing agent may be reduced by at least 1% by volume. In other embodiments it may be reduced by at least 20% by volume while in still other embodiments, it may be reduced by at least 40% by volume or 60%. In some embodiments, channels may be positioned vertically while in other embodiments, channels may be positioned at an angle or even horizontally.

In yet another exemplary embodiment, the process of the present invention is directed to reducing solid waste volume. The process involves loading organic material into a vessel. The vessel has a first zone and a second zone and at least one oxidizing agent is supplied in the first zone in the presence of an aqueous medium. The oxidizing agent oxidizes and breaks down at least a portion of the organic material. The organic material and oxidizing agent are agitated in the vessel to further break down the organic material.

Other features and advantages of the present invention will be apparent from the following description.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Repeat use of reference characters in the present specification and drawings is intended to represent same or analogous features or elements of the present invention.

DETAILED DESCRIPTION OF PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations and their equivalents.

In one embodiment, the present invention is generally directed to a two phase method that converts predominantly organic waste materials into useful byproducts. Following certain mechanical processing, the first conversion of the waste requires contacting the selected waste material with a strong oxidant to degrade organic materials to a bioconvertable substrate. The second conversion comprises respiration, fermentation, or photosynthetic metabolism of the substrate by an organism to yield a specific product. For example, complex plant hydrocarbons such as lignocellulose constitute a significant portion of municipal solid waste. Ozonation of this waste oxidizes the complex hydrocarbon to a substrate that includes simple saccharides. The saccharides can be bioconverted by microorganisms such as yeast or bacteria to yield an alcohol (ethanol), which is a useful industrial/commercial product. It should be understood, however, that many other waste materials may be processed according to the present invention and many other various useful products can be formed.

Figure 1:
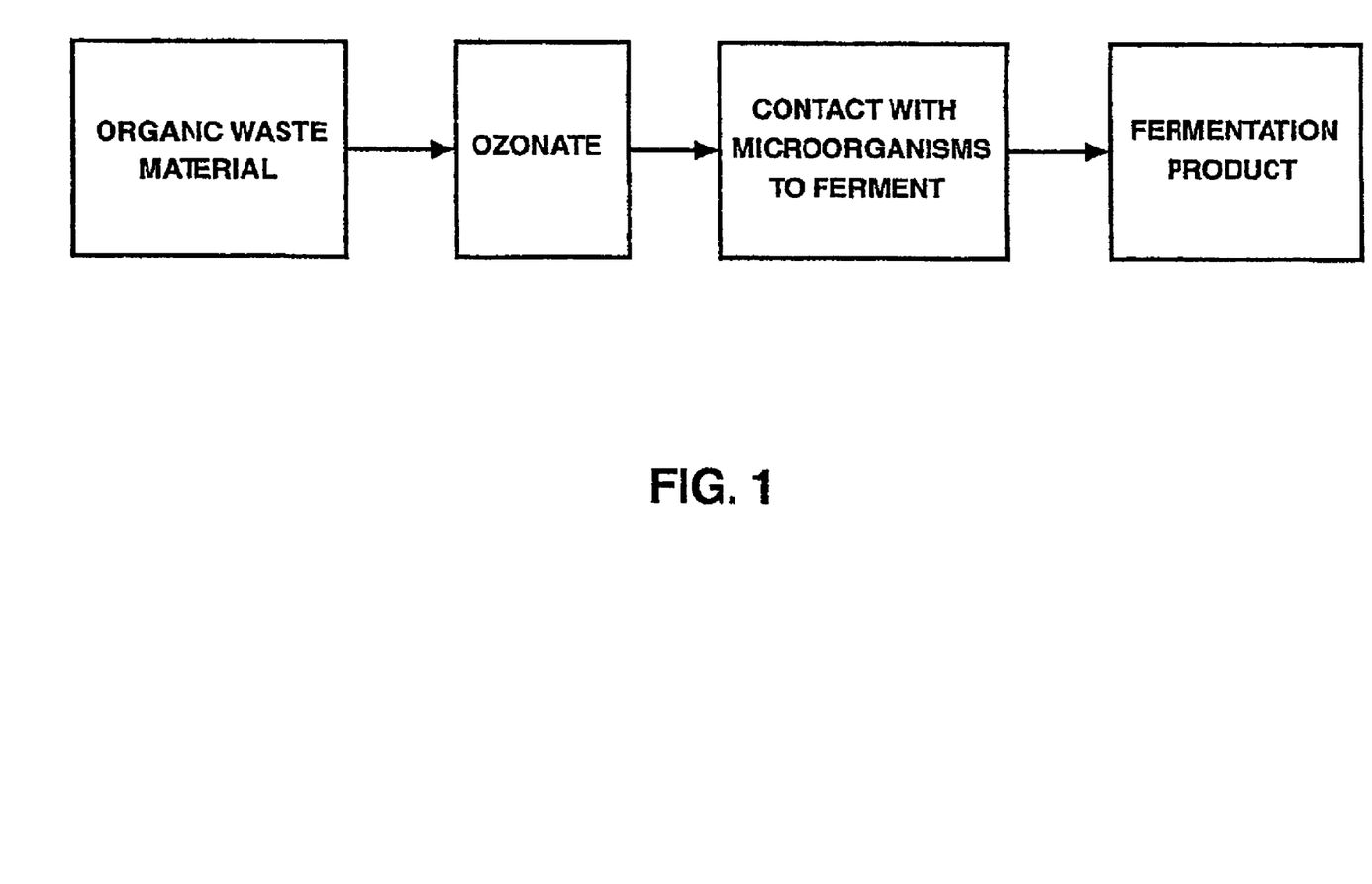
FIG. 1 is one embodiment of a flow chart of a process for converting organic waste materials into a useful product.

As used herein, waste(s) refers to any substance that is no longer desired in its present state or location. One embodiment of a general flow diagram of the process of the present invention for converting waste materials is illustrated in FIG. 1. Waste material 100 is pretreated and mixed with water to form a mixture 106. The mixture 106 is ozonated thereby converting some of the mixture to a substrate or medium 110. Substrate 110 is either prepared for commercial distribution 116 or is further processed by contact with an organism(s) 112 yielding a product 114. If prepared for commercial distribution as shown in 116, the product can be dried if desired. The dried ozonated product can be used in many useful applications, such as a fertilizer, even when not later contacted with organisms for bioconversion.

As will be described in more detail below, many and various diverse products can be produced according to the present invention. Depending on the product formed or created, the product can be collected, further processed as necessary, packaged, and then used as desired. For example, in one embodiment, the product formed according to the present invention can be ethanol, which can be distilled and used as an energy source. In another embodiment, the process of the present invention can be used to produce methane or another hydrocarbon gas.

As shown, according to the present invention, various waste materials are first collected. The organic waste materials are particularized, if necessary, and placed in water to create a mixture, and subsequently contacted with ozone. If desired, the waste materials can be pre-sorted or pre-separated prior to contact with ozone. For example, in one embodiment, inorganic materials, such as glass, metal, etc can first be removed prior to contact with ozone.

The ozone oxidizes the waste materials into a substrate that can sustain biological metabolic processes such as fermentation, respiration or photosynthesis. In particular, once contacted with ozone, the organic compounds are converted into substrates such as saccharides (sugars), that can be used as a growth medium for organisms. Alternatively, the oxidized waste can be contacted with a selected enzyme for conversion into a useful product.

After ozonation, the substrate is either collected for further processing or directly contacted with one or more specific organism or enzyme. As used herein, "organism" refers to any prokaryotic or eukaryotic organism including macro- and microorganisms and tissue culture. An organism used in the present invention can be a plant, a protista such as bacteria, a monera, or a fungus. The present invention also encompasses the use of genetically engineered organisms and microorganisms. The organisms carry out growth and metabolism thereby yielding a cellular product. As used herein, a cellular product refers to any intracellular or extracellular product produced by any respiratory (aerobic or anaerobic), fermentative, photosynthetic or any similar growth process. In general, fermentation can be defined as an ATP-generating metabolic process in which organic compounds serve both as electron donors (becoming oxidized) and electron acceptors (becoming reduced). Respiration is an ATP-generating metabolic process in which either organic or inorganic compounds serve as electron donors (becoming oxidized) and inorganic compounds serve as the ultimate acceptors (becoming reduced). Photosynthesis refers to the conversion of energy from light to chemicals.

In accordance with the present invention, the organisms used in the process can be carefully selected so as to promote the production of a desired product. For example, in one embodiment, organisms can be selected that will convert the organic waste materials into ethanol. The ethanol produced according to the process can be collected and used. For example, ethanol is known as an effective energy source.

Various organisms can be used to convert the oxidized waste materials into ethanol. As described above, the organism can be a prokaryotic or a eukaryotic organism. One example of a bacterium that is known to produce ethanol from hydrocarbons is *Zymomonas mobilis*. An example of a yeast that is known to produce ethanol is *Saccharomyces cerevisiae*. It should be understood, however, that various other organisms known to produce ethanol can also be used in the process of the present invention.

It should be understood, however, that besides ethanol-producing microorganisms, other organisms can be selected so as to produce other types of microbial products. Such products include, but are not limited to, other alcohols such as alcohols containing one to nine, or greater, carbon atoms. Particular examples of alcohols that can be produced according to the process of the present invention include propanol, butanol, pentanol, hexanol, heptanol, octanol and nonanol. Besides alcohols, other products that may be produced include alkanes, aldehydes, ketones, organic acids and the like. The products described herein are presented as examples but not as limitation of the potential bioconversion products of organism growth on substrate.

The process of the present invention can also be used to form pharmaceuticals. Such pharmaceuticals can include vitamins, such as vitamin C. Other products include microbial cellulose and other useful polymers. Further, the process can also be designed to promote the production of lactic acid. Lactic acid can be used to produce, for example, biocompatible polymers. Other bioconversion processes include but are not limited to a two stage conversion process using yeasts with *Acetobacter* or *Gluconobacter* species for producing acetic acid. Growth of *Propionibacterium* on carbohydrates yields propionic acid. Microbial protein may be produced by growth of microorganisms on the oxidized substrate. Bacteriocins, unique antimicrobial proteins, may be produced by a wide variety of prokaryotic microorganisms grown on the substrate.

Other products of the present invention can include purines, pyrimidines, proteins, phospholipids, lipids, beta glucans produced from yeast, enzymes and pigments. One skilled in the art will recognize that these products may be integral components in the cell structure or, in some instances, particularly for the enzymes and pigments, may be excreted from the cell. Cell products may be the cells themselves such as valuable tissue culture organisms. Additional cellular products can include alkanes, alkenes, alkynes and cyclic versions of these. Esters, amines, amides, cyclic and aromatic compounds, alkanes, alkenes, alkynes, and gums may be produced by a variety of organisms. Ethers, although less common, are produced by certain organisms. Peroxides, such as hydrogen peroxide are produced by certain bacteria.

Phospholipid is produced by many organisms, particularly in cell bound membranes. A variety of lipids, including hydroxybutyrate and hydroxyvalerate are produced by eukaryotic and prokaryotic organisms. These lipids have commercial value as starting materials for further syntheses. A number of organisms including but not limited to bacteria, yeast, fungi, and algae, produce pigments of commercial and scientific importance. Certain of these pigments are of use in research or in commercial manufacturing.

A wide variety of aromatic compounds are produced by growth processes of a variety of prokaryotic and eukaryotic organisms. Commercially valuable gums are produced by growth of organisms including but not limited to *Xanthomonas* sp. which produces xanthan gum. A number of enzymes may be produced by growth of selected prokaryotic and eukaryotic organisms on the substrate including but not limited to: amylases produced by species of *Aspergillus, Rhizopus* and *Bacillus*; catalase produced by species of *Micrococcus* and *Aspergillus*; cellulase produced by *Trichoderma* and *Aspergillus*; β-galactosidase (lactase) produced by *Kluyveromyces marxianus* and *Aspergillus;* invertase produced by *Saccharomvces cerevisiae* and *Candida utilis*; and lipase produced by *Aspergillus, Rhizopus, Penicillium* and *Candida*. Using eukaryotic organisms to bioconvert the substrate can yield a wide variety of products including pigments from algae, single cell protein from yeasts, DNA and RNA and other complex polymeric compounds. One skilled in the art will recognize that the above mentioned products may be produced as a result of respirative, fermentative or photosynthetic metabolic and anabolic pathways. The preceding bioconversion processes described herein are presented as examples but not as limitation of the potential bioconversion processes of organism growth on substrate.

As mentioned above, in one embodiment of the present invention, the oxidized waste materials can be fed to various plants, such as algae, for harvesting products produced by the plants. For example, in one embodiment, once the materials are oxidized, the oxidized medium can be fed to red algae, also known as *Rhodophyta*, in order to produce pigments. Specifically, red algae are red due to the presence of the pigments Phycocyanin and Phycoerythrin. Both Phycocyanin and Phycoerythrin fluoresce at a particular wavelength. Thus, the pigments are particularly useful for research. In addition, red algae contains high vitamin and protein content, making it attractive as a possible food source for animals and/or humans.

Besides red algae, another plant that can be grown from the oxidized medium is *Gelidium purpurascens*, which is a bright red seaweed. *Gelidium purpurascens* can be used as a source of agar for bacterial media, foods, etc.

Another useful substance that can be obtained from algae, such as Rhodophytes and Kelps is alginate. Alginates are gum-like substances that can be used in many useful and diverse applications. For example, alginates have an affinity for water and are commercially important in the production of paper, toothpaste, beer and frozen foods.

In still another embodiment of the present invention, the oxidized waste materials can be fed to an organism for the production of hydrocarbons, such as methane gas. As the methane gas is produced, the gas can be collected and used as a fuel source. For example, in one embodiment, the oxidized waste materials can first be converted into ethanol as described above. Once produced, the ethanol can then be fed to a microorganism which is adapted to convert ethanol into methane. An example of a genus of methane-producing bacteria is *Methanobacterium*.

In some applications, it should also be understood that the oxidized waste materials can be fed directly to a microorganism for the production of hydrocarbon gases.

Any recalcitrant organic molecule of biological or synthetic origin can be processed and converted according to the present invention. In other words, any organic material that can be oxidized may be used to produce cellular products as described above. Such organic waste materials can include municipal solid waste, restaurant and/or other food waste, discarded cotton products, animal waste materials, sewage, petroleum refining wastes, chemical manufacturing wastes, old tires, proteinaceous wastes, carbohydrate-containing wastes, lipid-containing wastes, pesticides, and waste water. Further, the organic waste materials can include any complex organic compounds such as lignin and lignocellulosic materials, proteinaceous materials such as cheese whey, any carbohydrates, lipids, chitin and chitosan materials, food processing plant waste, gums such as guar gum, oat hull, barley, hay, corn stover, corn stillage, bagasse, paper pulp, paper sludge, softwood and hardwood residues, and the like.

Depending upon the materials being processed, in one embodiment, the waste materials can first be pre-separated for removing, for instance, inorganic materials from the materials to be processed. Besides being pre-separated, the materials can also be sized prior to being contacted with ozone. For example, the waste materials can be ground, milled or pulverized as desired. Reducing the size of the waste materials will create more surface area to facilitate processing.

Once the waste materials have been selected and collected, the materials are ozonated. This process degrades the organic compounds contained in the materials into smaller organic compounds. In general, ozonation is carried out in an aqueous medium. As such, if desired, the waste materials can be combined with water prior to ozonation.

Many different methods can be used in order to contact the waste materials with ozone for decomposing the organic compounds. For example, in one embodiment, the waste materials can be contained within a tank and ozone can be fed toward the bottom of the tank and bubbled through the mixture. An example of this embodiment is described in the present inventor's prior application filed on May 27, 1999 and having U.S. Pat. No. 6,117,324, which is incorporated herein by reference in its entirety.

In one embodiment, if the waste materials are flowable, the waste materials can be fed through a line, such as a pipe, and contacted with ozone within the line. This embodiment is particularly well suited for use in continuous systems.

Figure 2:
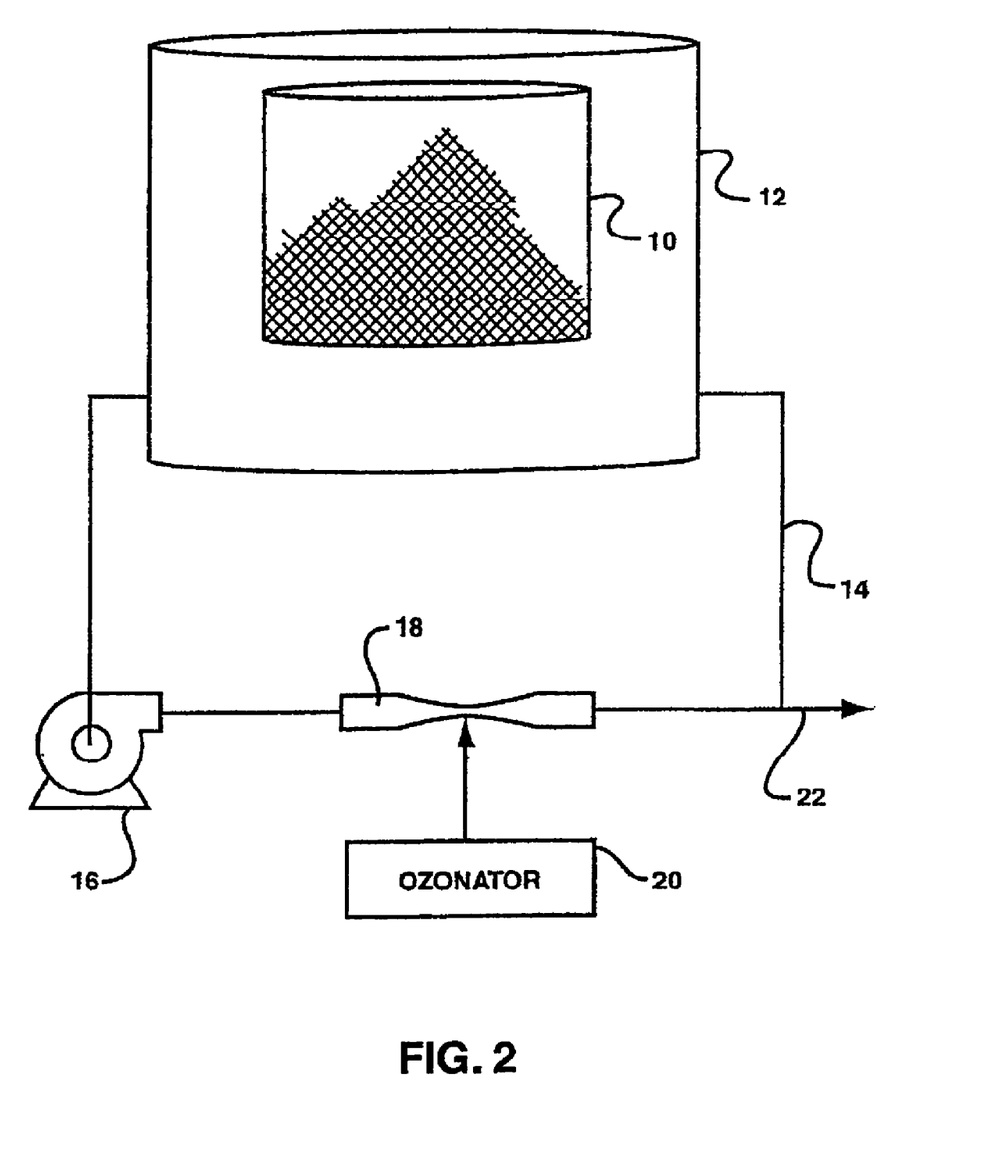
FIG. 2 is one embodiment of a process for ozonating organic waste materials.

An embodiment of a method for contacting the waste materials with ozone is illustrated in FIG. 2. As shown, in this embodiment, the waste materials are placed in a porous container 10. Porous container 10 can be constructed in various manners depending upon the size of the waste materials. For instance, the porous container can be made from a mesh or screen material or, alternatively, can be a solid structure with perforated walls.

As shown, porous container 10 is contained within a larger vessel 12. Vessel 12 contains a liquid such as water which is circulated around a circulation loop 14 via a pump 16. In this manner, the liquid flows through the porous container 10 causing organic compounds contained within the waste material to dissolve or be hydrated. Ozone is then fed into the circulation loop 14 for converting the organic waste materials into a fermentable medium. Residual ozone is transported via pump 16 back to vessel 12 where the ozone may contact organic compounds in container 10 to facilitate degradation of organic materials.

In this embodiment, in order to contact the mixture containing the organic compounds with ozone, the system contains a venturi 18 in communication with an ozonator 20. A venturi is generally described as a constriction that is placed in a pipe or tube that causes a drop in pressure as fluid flows through it. As shown in the figure, the venturi can include a straight section or a throat positioned in between two tapered sections. When used in the process of the present invention, the venturi draws the ozone into the main flow stream.

Using a venturi in the system of the present invention offers various advantages. For instance, the venturi allows the ozone to rapidly combine with water or the mixture containing the organic compounds. Thus, a maximum amount of ozone can be dissolved into the mixture. Further, better mixing between the ozone and the organic compounds is achieved using the venturi.

As shown in FIG. 2, once the mixture has been ozonated to an extent desired, the resulting solution can be discharged from the system through discharge line 22 for further processing in accordance with the present invention.

Figure 3:
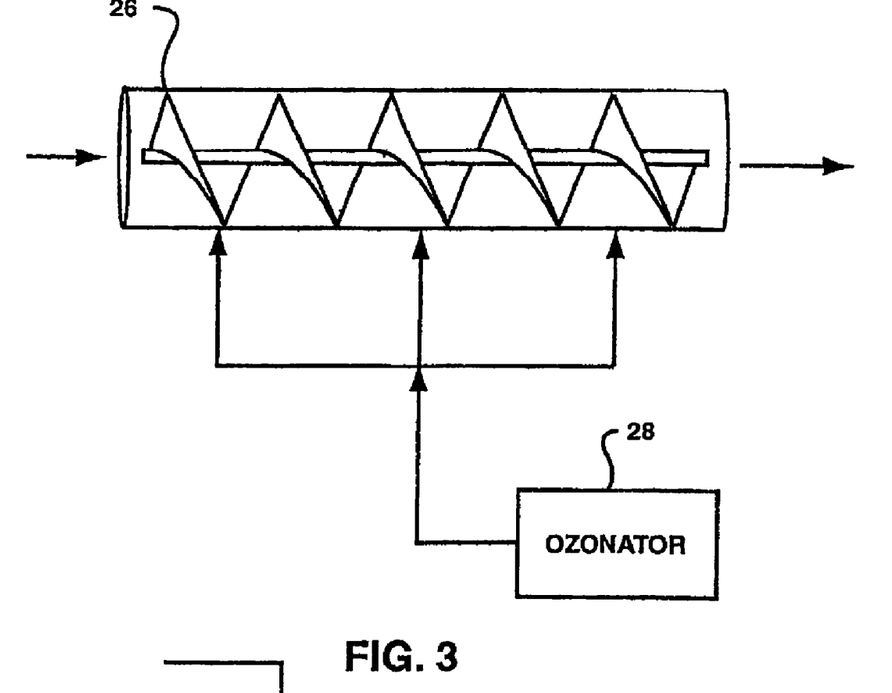
FIG. 3 is an alternative embodiment of a process for ozonating organic waste materials.

Referring to FIG. 3, still another embodiment of a system for treating waste materials with ozone is illustrated. In this embodiment, the system includes an auger 26 for receiving the waste materials. Auger 26 is configured not only to move the waste materials at a desired speed, but may also be is configured to reduce the size of the waste materials. As shown, the system further includes an ozonator 28 which feeds ozone into the auger to treat the materials. Ozone can be fed into the auger at a single location such as generally in the middle or, as shown, at multiple locations. Ozone also may be fed into the waste materials from one or more locations in the center of the auger shaft.

The embodiment illustrated in FIG. 3 is particularly well suited to ozonating waste materials that do not contain a substantial amount of fluids. For instance, the auger is well suited to receiving and sizing solid materials contained in a thick mixture.

In still a further embodiment of the present invention, ozonation of the waste materials can be carried out in a pressurized vessel. In this embodiment, a mixture or an aqueous solution containing the organic compounds can be placed in a vessel under pressure. Ozone can then be introduced into the chamber for breaking down the organic compounds.

The amount of ozone contacted with the waste materials will depend upon the particular application and the type of materials being treated. In general, the concentration of ozone contacting the waste materials should be at least 0.01 ppm. Preferably, however, greater concentrations of ozone are used during the process. For instance, for most applications, ozone should be fed at a concentration sufficient to saturate or to nearly saturate the mixture/solution with ozone.

The amount of ozone that it takes to saturate an aqueous solution depends upon the temperature and pressure of the solution. In general, greater amounts of ozone can be dissolved into the solution at lower temperatures. Thus, in one embodiment, the aqueous solution being treated in accordance with the present invention can be cooled prior to or during ozonation. For instance, in one embodiment, the temperature of the aqueous solution can be maintained below about 20° C., and particularly below about 15° C. The solubility of ozone in water at 20° C. is about 575 milligrams per liter, while the solubility of ozone in water at 10° C. is about 785 milligrams per liter.

In one embodiment, the solution or mixture being combined with ozone can first be cooled prior to or during ozonation. After ozonation, however, the solution or mixture can then be heated in order to cause the ozone to react more rapidly with the organic materials.

Similar to the concentration of ozone, the amount of time the waste materials are contacted with ozone also depends upon the particular application. For most applications, however, ozonation should continue until most of the organic compounds are broken down into smaller hydrocarbon species capable of being used in cellular processes. The length of time ozonation should occur in the process of the present invention can be determined using various methods. For example, in one embodiment, the maximum sugar potential of the waste materials can first be determined. Sugar potential can be determined by first pretreating a sample of the waste materials for different times in order to release the sugars and then conducting the Fehlings Test for reducing sugars on the sample. Once the maximum sugar potential for the waste materials is determined, the waste materials can be contacted with ozone at a concentration and for a time sufficient for the maximum sugar potential to be achieved.

In an alternative embodiment, the amount of sugars can be monitored during the ozonation process by collecting periodic samples and conducting the Fehlings Reducing Sugar Test. The amount of sugar generated then can be plotted versus time of ozonation. A maximum amount of reducing sugar is achieved upon reaching a maximum peak or steady state as indicated by the plot. When the slope of the line indicates a decline in sugar content over time, it is indicative of additional ozone continuing to oxidize and, thereby destroy the newly formed sugars. Further ozonation may then result in the reduction of useful medium and degrade the quality of the resultant substrate.

Besides testing for sugars, it is also possible to determine how much ozonation is required in a particular application by testing for the amount of degradation of proteins in the waste materials. This can be tested by any of a number of methods including the Bradford method, gel filtration (molecular sieve, molecular size exclusion) methods and polyacrylamide gel electrophoresis methods. Similar tests to determine optimum ozonation can be conducted for other chemical moieties such as lipids.

During ozonation, the pH of the aqueous solution may have a tendency to alternatively decrease and increase with a gradual overall downward trend. Should the pH of the solution vary too greatly from neutral (generally between a pH of 5 and 9), subsequent cellular growth may be adversely affected depending on the organism cultured. Consequently, in some applications, a base or an acid can be added to the aqueous solution prior to or during or after ozonation to adjust pH to the optimum pH range for the microbial population.

Prior to or after ozonation, various enzymes can also be added to the aqueous solution to assist in breaking down the waste materials. For instance, if the waste materials contain cellulosic materials, cellulase enzyme can be added to the materials. The enzyme will break down cellulose increasing the availability of organic compounds that may be released during the process of the present invention. Other enzymes that can be added include lipases, proteases, amylases, and the like.

Once the aqueous solution containing the waste materials has been ozonated, the remaining solid materials can be separated, if desired, from the aqueous solution by a variety of means including but not limited to settling, centrifugation, and filtering. Separating the materials, however, can occur prior to ozonation or after contact with organisms.

As described above, once the mixture of waste materials has been ozonated, a solution is produced containing a growth medium (substrate) for organisms. The substrate can contain, for instance, sugars, proteins, lipids, inorganic compounds, minerals, vitamins, and other nutrients. In accordance with the present invention, the oxidized medium is then contacted with organisms and/or enzymes for carrying out the processes of growth, metabolism and bioconversion via fermentative, respirative, photosynthetic, or similar pathways. In accordance with the present invention, particular organisms can be selected for producing cells or specific end products that can be collected and used as desired. For example, in one embodiment, microorganisms can be selected that will convert the fermentable compounds contained within the aqueous solution into ethanol. The ethanol can then be collected and separated from the solution and used, for instance, as an energy source.

The particular organisms and/or enzymes selected for carrying out respiration, fermentation, photosynthesis and other cell processes will depend upon the particular application and the desired products. The organisms can be, for instance, yeast, fungi, molds, bacteria, algae or genetically engineered microorganisms or tissue culture or mixtures thereof.

The manner in which the organisms are supplied with the oxidized medium can also vary. For instance, in one embodiment, a batch system can used in which the aqueous medium is placed into a reservoir containing the organisms. The aqueous substrate can remain in contact with the organisms until microbial growth and metabolism has reached the desired endpoint.

Figure 4:
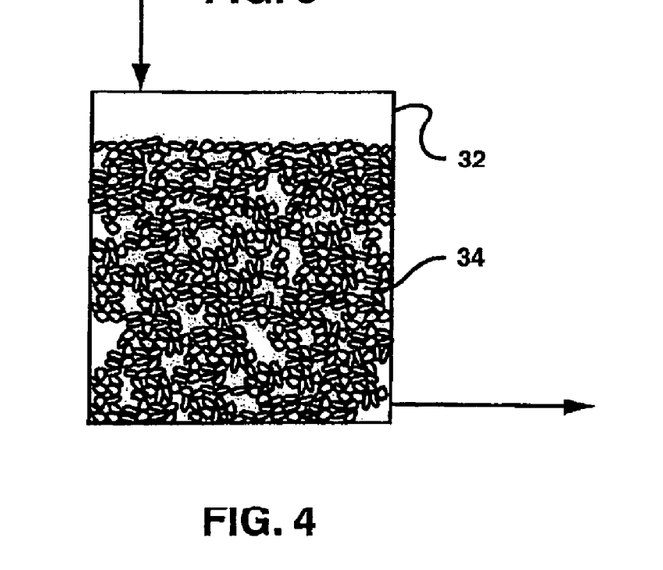
FIG. 4 is one embodiment of a process for contacting ozonated waste materials with microorganisms for causing fermentation or another metabolic process.

In another embodiment, the ozonated solution can be fed through an immobilized culture of organisms. For instance, as shown in FIG. 4, the ozonated solution can be fed to a packed tower 32. Packed tower 32 can contain a packing material 34 in which the organisms reside or are bound to the outer surface. The ozonated solution (substrate) can be filtered through the packing material for carrying out fermentation and/or other growth processes. Depending on the cellular product produced, the resulting fluid or gas can be collected from the tower.

In still another embodiment, the organisms can be contained in an aqueous culture that continuously contacts the ozonated solution in a continuous culture, chemostat-type process. For example, in this embodiment, the ozonated solution can be fed into a chemostat chamber which contains a solution comprising organisms. Fermentation and other growth processes can occur within the chemostat chamber as the organisms conduct metabolism. Excess solution containing the desired organism and/or product can be collected.

After contact with the organisms, the cellular products can be separated from the aqueous solution, if desired. For instance, when producing ethanol, ethanol can be distilled from the remainder of the solution. In some embodiments, however, it may not be necessary to separate the microbial products from the remainder of the solution.

Depending on the product that is produced according to the present invention, various post processing steps can be carried out. For instance, depending on the product, the product can be collected, stored and packaged as desired. For example, in one embodiment, the product can be dried and then packaged prior to being shipped to a desired location.

In one embodiment, the microbial products can be separated from the solution and the remaining solution can be fed to plants for plant growth. For example, some waste materials such as animal waste contain relatively high concentrations of fertilizing nutrients, such as nitrogen, phosphorous and potassium. These nutrients are typically contained in the oxidized medium. A portion of these nutrients may be used by the organisms introduced to the medium. However, in the case of high fertilizing nutrient content, residual nitrogen, phosphorus and potassium compounds may remain in the spent medium. In accordance with the present invention, the spent substrate solution can then be fed to the plants that will beneficially remove these nutrients from the solution. If desired, the spent medium can be re-ozonated prior to being fed to the plants.

In general, the solution can be fed to any suitable plant or crop. In one embodiment, the solution can be fed to a wetland for use by any vegetation that may be present in the wetland. A wetland is typically defined as a foliage and vegetation area that is configured to accept runoff.

Alternatively, the solution can be fed to plants in a hydroponic system. A hydroponic system involves growing plants in a soil-less system, usually in a liquid medium that provides all essential minerals.

In still another embodiment, the solution can be used as irrigation water. For example, the solution can be sprayed over a field or, alternatively, used to irrigate plants grown in greenhouse flats or similar containers.

As described above, besides ethanol, various other fermentation and microbial growth products can be made according to the present invention. In general, the microbial product can be any cell bound or cell excreted product. For example, the process of the present invention can be used to produce lactic acid or pharmaceuticals. Other fermentation and microbial products that may be produced include other alcohols, aldehydes, ketones, organic acids, polyhydroxy compounds such as polyhydroxybutyrate and polyhydroxyvalerate, proteins and single cell proteins, enzymes and pigments. Cellular products can include the cells per se, pigments, phospholipids. Other cellular products can include esters, ethers, amides, amines, purines, pyrimidines, alkanes, alkenes, alkynes, cyclic and aromatic compounds, gums, microbial cellulose and other polymers.

In another embodiment, the process of the present invention is directed to reducing landfill mass with or without production and collection of a useful product. In this embodiment, the process involves creating at least one channel 72 in a landfill mass 70 at a landfill site and supplying at least one oxidizing agent 74 in the presence of an aqueous medium into the channel. Suitable oxidizing agents 74 include ozone and hydrogen peroxide. However, many other oxidizing agents 74 could also be used and combinations of different oxidizing agents 74 may also be utilized. A landfill mass 70 contains carbonaceous materials and the oxidizing agent 74 oxidizes and breaks down a portion of these materials. In some embodiments, after the oxidizing agent 74 is added, at least one species of microorganism 44 is supplied into the channel 72 and the microorganism 44 consumes the oxidized carbonaceous matter.

Figure 5A:
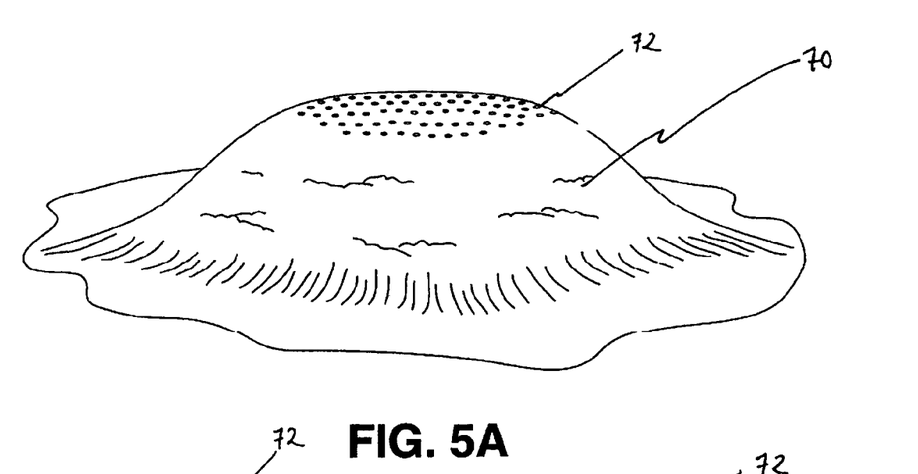
FIGS. 5A-5G depict one embodiment of a process for reducing landfill mass by contacting ozonated waste materials with microorganisms.
Figure 5B:
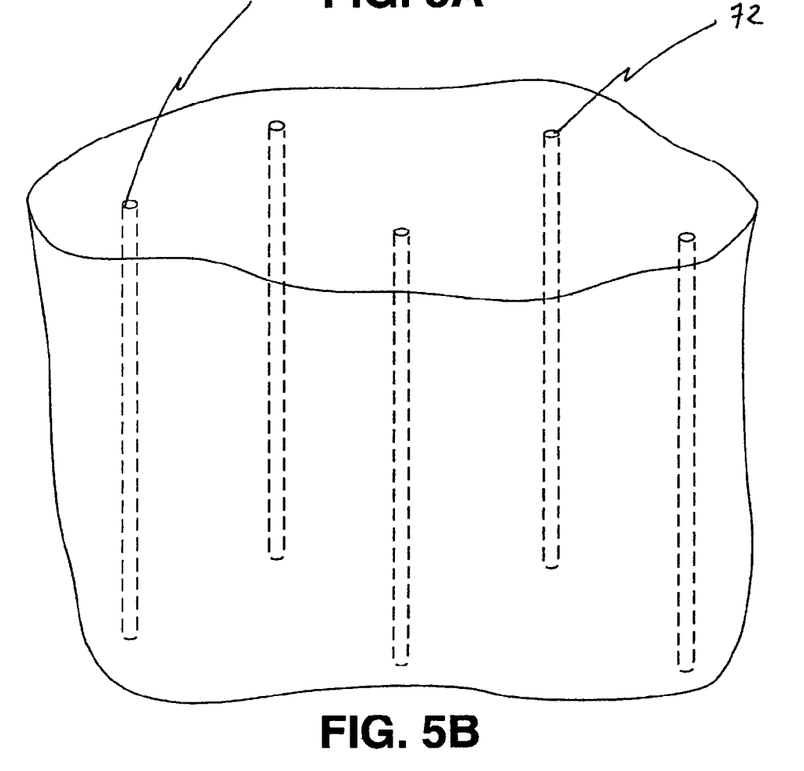

In one embodiment, a plurality of channels 72 are created within a landfill mass 70 so that the oxidizing agent 74 can contact the mass. A process for reducing the landfill mass 70 utilizing channels 72 is illustrated in FIGS. 5A-5G. At least one channel 72 is created in the landfill mass 70 as shown in FIG. 5A. The landfill mass 70 may be located anywhere but in some embodiments the landfill mass 70 is located at a landfill site. The landfill mass 70 can also contain a plurality of channels 72 as illustrated in FIG. 5A and more closely illustrated in FIG. 5B. The channels 72 can be created at any suitable depth and diameter to allow the oxidizing agent 74 to penetrate the landfill mass 70. The channels 72 may have a depth of at least 1 foot and a diameter at least 0.5 inches. The channels 72 are spaced between 6 inches and 20 feet apart. However, it should be understood that the channels 72 could be spaced any distance apart from one another so as to allow for maximum contact of the landfill mass 70 with the oxidizing agent 74.

Figure 5C:
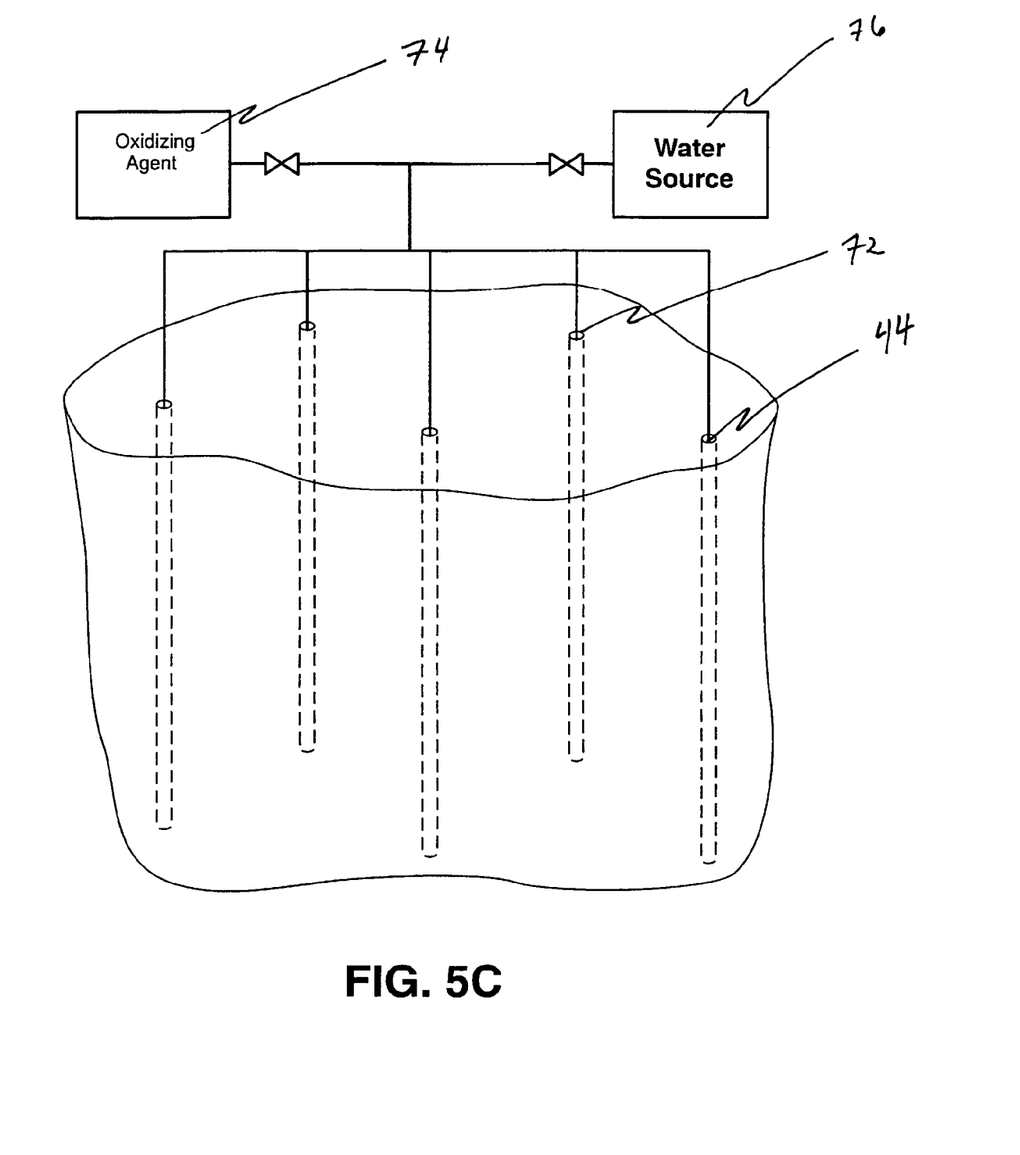
Figure 5D:
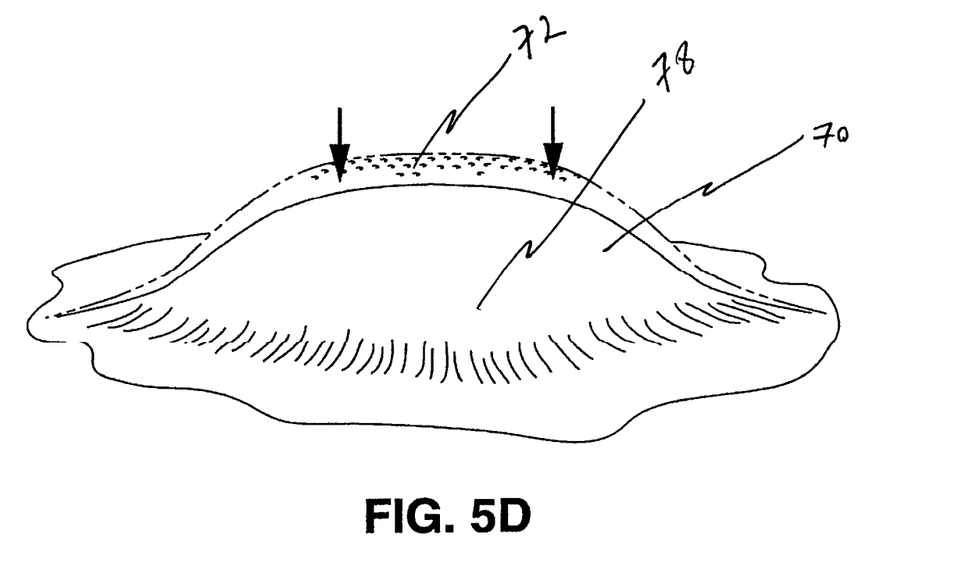
Figure 5E:
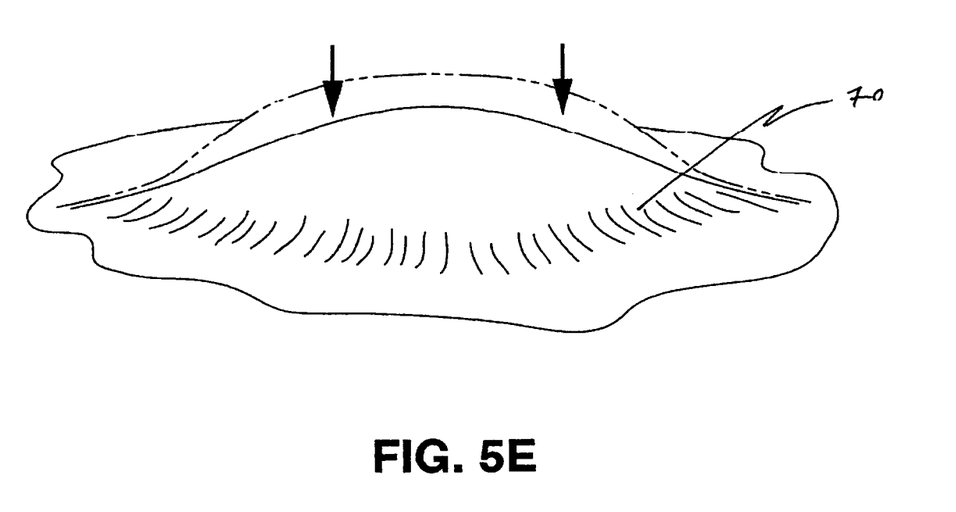
Figure 5F:
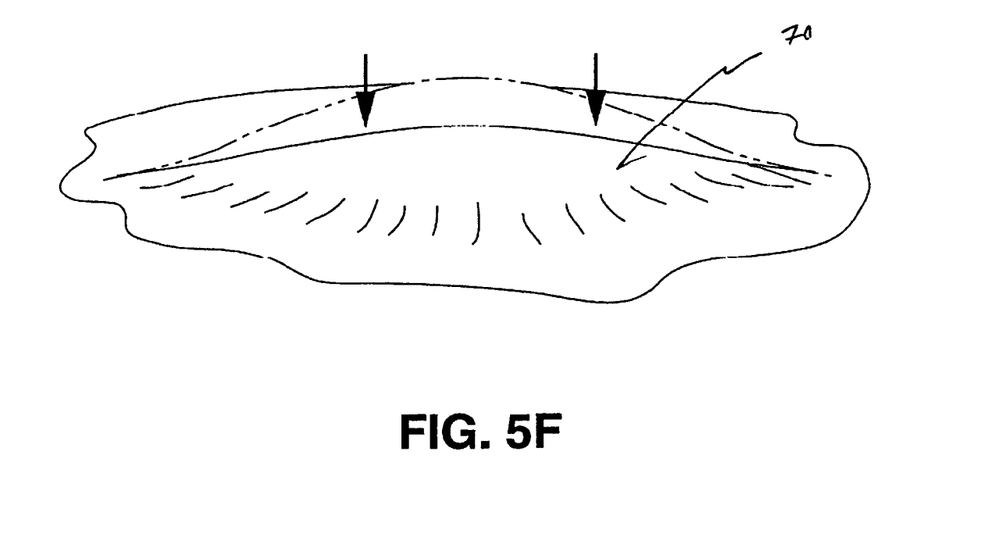
Figure 5G:
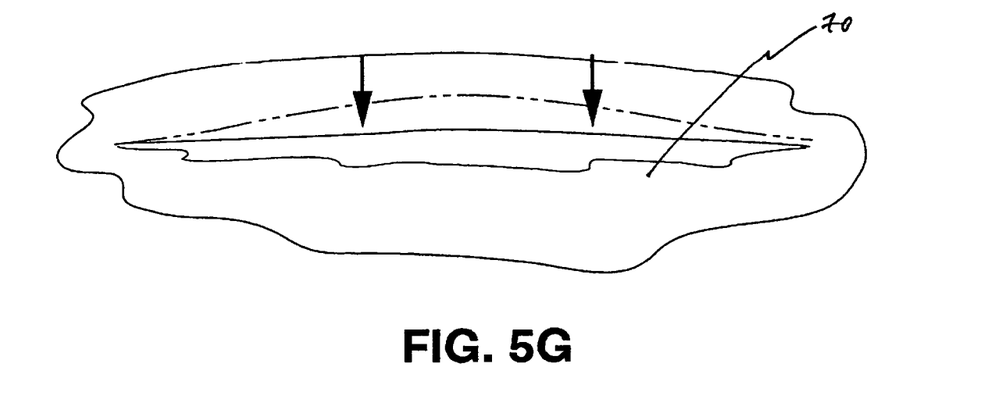

The oxidizing agent 74 can be added to the channels 72 in the presence of an aqueous medium 76 as illustrated in FIG. 5C. A suitable aqueous medium 76 is water. Once the oxidizing agent 74 is supplied in a channel 72, it serves to oxidize and break down at least a portion of the organic materials present in the landfill mass 70.

In some embodiments, microorganisms 44 are supplied into the channels 72 to consume the organic materials. Such microorganisms 44 include but are not limited to *Ruminococcus, Cellulomonas, Psuedomonas, Acetobacter, Lactobacillus, Lactococcus*, and *Alcaligenes*. Suitable microorganisms 44 may include fungi or bacteria and particularly aerobic microorganisms. One or more species of microorganisms 44 can be supplied with the result being that the oxidizing agent 74 and microorganism 44 reduce the landfill mass 70 (as illustrated in FIGS. 5D-5G).

Additional channels 72 may be added after the initial supply of oxidizing agent 74 and/or microorganisms 44. Additional oxidizing agent 74 can also be added after the initial supply as can additional microorganisms 44. Various concentrations of oxidizing agent 74 and microorganism may 44 be suitable depending on the size of the landfill mass 70 as well as the quantity of organic materials present in the landfill mass 70. Also, various methods of adding oxidizing agent 74 and microorganism 44 to the channels 72 will be suitable such as a venturi 18 described previously in another embodiment of this invention. In an exemplary embodiment of the process described herein and illustrated in FIGS. 5A-5G, the reduction in volume of the landfill mass 70 is at least 1% by volume. However, the reduction of volume may be greater or less than this amount depending on the particular conditions present.

In some embodiments, air may be added into channels 72 to promote the growth of aerobic microorganisms and to help speed the degradation of the landfill mass 70. However, in conditions favorable to growth, temperatures may increase quickly as a result of the rapid proliferation of microorganisms 44. In some embodiments, the heat produced from the rapid proliferation of microorganisms 44 may be recaptured. Such a method of recapturing heat may include utilizing tubes or pipes to redirect heat away from the rapid proliferation of microorganisms.

In certain embodiments, a temperature sensor 78 may be placed in the landfill mass 70 to detect such rapid changes in temperature. If needed, various methods may be utilized to slow growth of the microorganisms 44 and decrease the temperature of the landfill mass 70. One such method that may be utilized with aerobic microorganisms 44 involves adding a gas into the channels 72 which will create anaerobic conditions. Gases such as carbon dioxide or nitrogen would be suitable to create anaerobic conditions.

In certain embodiments in which the process of the present invention is directed to reducing landfill mass with the production of a useful product, the product can include carbon dioxide which can be redirected to a landfill mass 70 to create anaerobic conditions. In such embodiments, the temperature sensor 78 may trigger the release of such product to slow the growth of the microorganisms.

Figure 6:
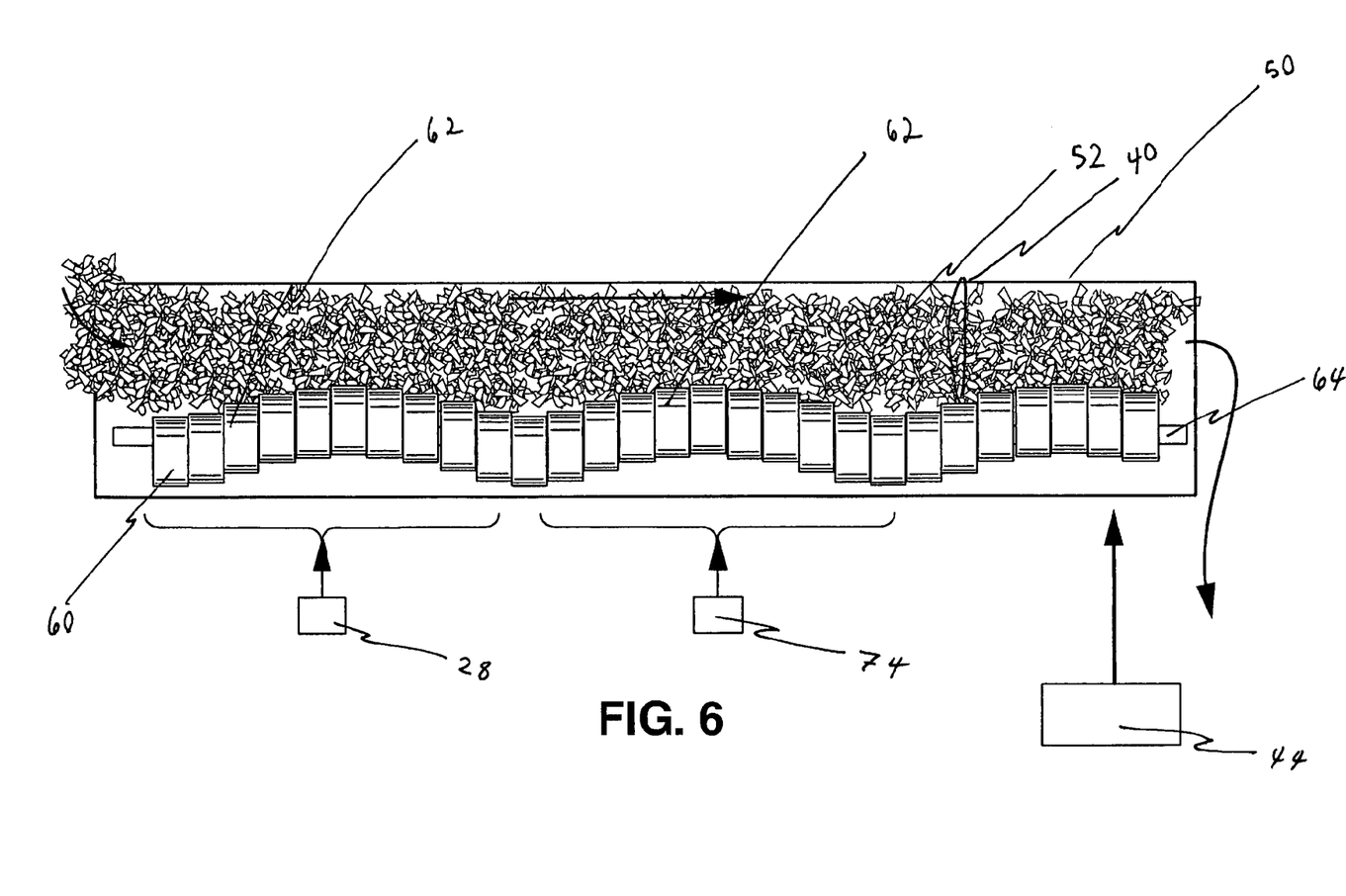
FIG. 6 depicts one embodiment of a process for reducing solid waste volume through peristaltic action.
Figure 7:
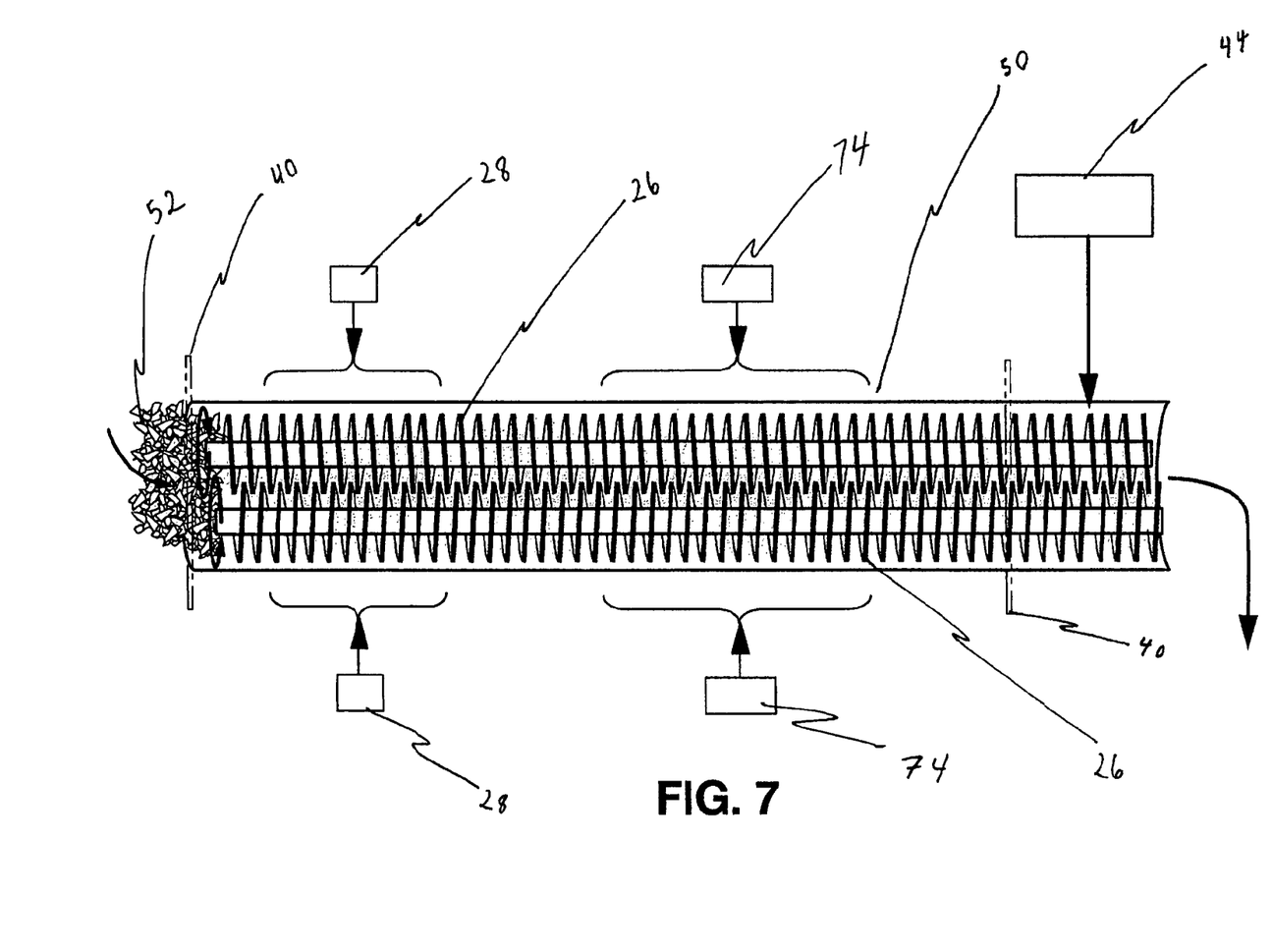
FIG. 7 depicts one embodiment of a process for reducing solid waste volume by utilizing an auger.
Figure 8:
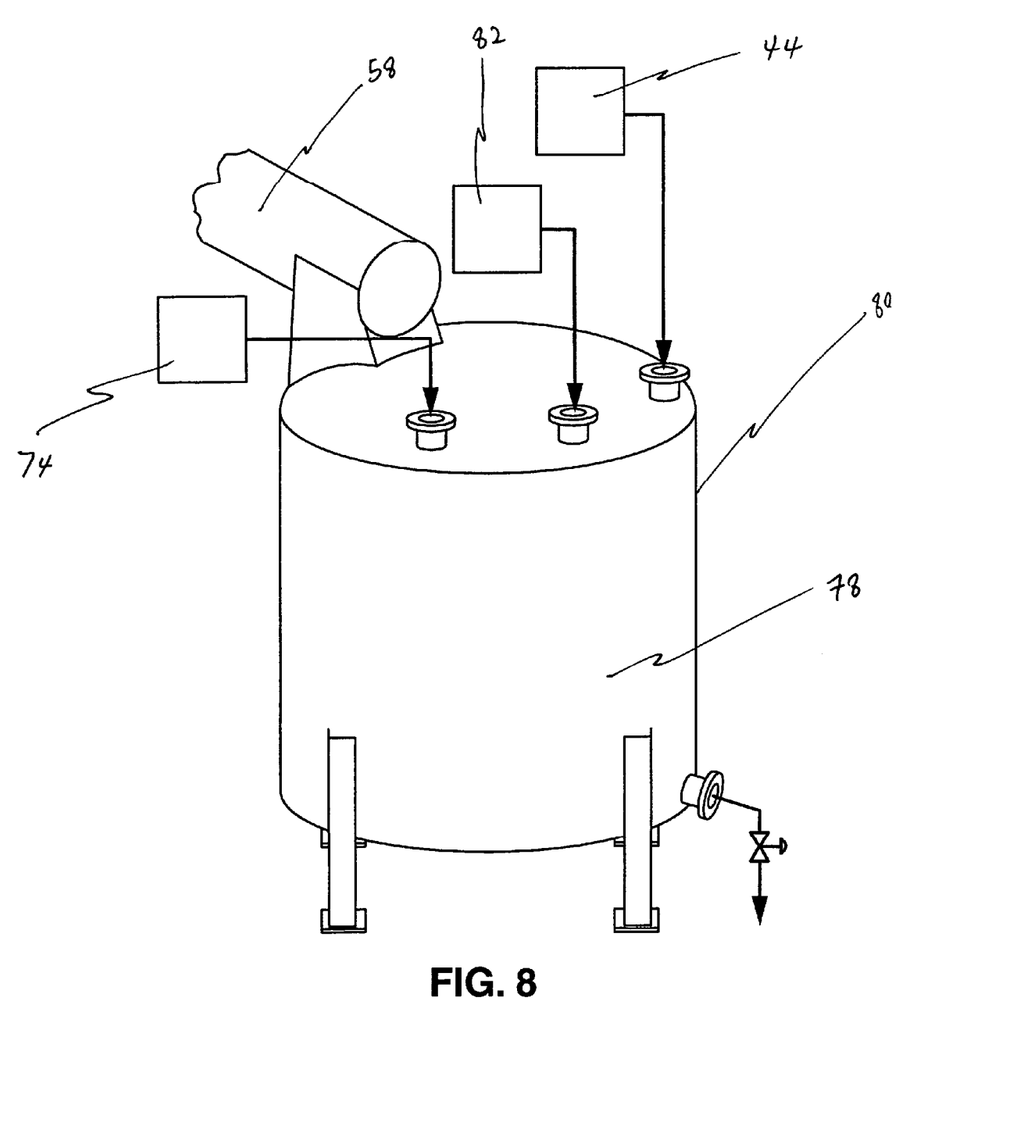
FIG. 8 depicts one embodiment of a process for reducing solid waste volume by utilizing a bioreactor.

In another embodiment, a process for treating waste materials 52 with at least one oxidizing agent 74 and thereby reducing the volume of the waste materials 52 is illustrated in FIGS. 6, 7, and 8. Waste materials 52 are loaded in a vessel 50. The volume of waste material 52 can vary depending on the amount of waste being processed. The vessel 50 can be made up of one or more zones or regions. The oxidizing agent 74 can be fed into the vessel 50 at a single location or at multiple locations and may be fed in at designated zones or regions. If necessary, directional fans can be used to force the oxidizing agent 74 throughout the vessel 50. As stated before, suitable oxidizing agents 74 include ozone and hydrogen peroxide. However, many other oxidizing agents 74 could also be used and combinations of different oxidizing agents 74 may also be utilized. As shown, the process further includes an ozonator 28 which feeds ozone into the vessel 50 to treat the materials. In some embodiments, the oxidizing agent 74 can be injected into the waste material 52 as ozonated water as well as via gaseous ozone and oxidizes and breaks down at least a portion of the waste materials 52. The waste material 52 is also agitated to further oxidize and break down the organic material. A hot air curtain 40 can be installed at the entrance of the vessel 50 to prevent backflow of the oxidizing agent 74 and may also be positioned within the vessel 50 to destroy oxidizing agent 74 prior to the addition of microorganisms 44.

In some embodiments, microorganisms 44 are added to vessel 50 after dissipation of any remaining oxidizing agent 74. The microorganisms 44 consume the oxidized waste material 58 which results in an eventual reduction of volume of the solid waste. The processed waste materials 52 are then removed from the vessel 50.

In some embodiments, the vessel 50 may be located on a vehicle such as an automobile or a trailer. Such placement would be advantageous because it would allow the vessel 50 to be transported to areas where waste material is collected. The vessel 50 may also be permanently located in areas where waste material 52 collection takes place.

As shown in FIG. 6, peristaltic action 60 may be utilized to agitate the waste material 52. In this embodiment, the process involves various leaves 62 which are attached to a cam shaft 64 within a vessel 50. The cam shaft 64 turns and causes the leaves 62 to move in and out of the vessel 50. The leaves 62 move in a sigmoidal wave causing peristaltic action. Peristaltic action involves successive waves of contraction which causes the waste material 52 to move forward at a desired speed. The oxidizing agent 74 may also be fed into the waste materials 52 from one or more locations between the leaves 62. The peristaltic action causes the waste material 52 to mix more effectively with the water and oxidizing agent 74. In addition to the hot air curtain 40 previously described, hot air may 82 also be pulsed between leaves 62 to force free radical oxygen to be released from the oxidizing agent 74 and to destroy the remaining oxidizing agent 74 prior to exit.

As shown in FIG. 7, augers 26 may be utilized to agitate the waste material 52. In this embodiment, the process includes multiple augers 26 for receiving the waste materials 52 positioned inside a vessel 50. The augers 26 have a scissor action via serrated edges and slice waste materials 52 as the blades pass one another. The augers 26 are configured not only to move the waste materials 52 at a desired speed, but may also are configured to reduce the size of the waste materials 52. The augers 26 are fast turning but the pitch of the blades is shallow to allow for slow forward movement of the waste materials 52. Oxidizing agent may also be fed into the waste materials 52 from one or more locations in the center of the auger shaft. It may be useful to heat the waste materials 52 after the oxidizing agent 74 is fed into the vessel 50 to force free radical oxygen to be released, thereby forcing an oxidation reaction.

As shown in FIG. 8, a bioreactor 80 may be utilized to reduce solid waste volume. In this embodiment, oxidized waste material 58 is removed from the vessel 50 and supplied into a bioreactor vessel 80. Thereafter, microorganisms 44 are supplied into the bioreactor 80 to consume the oxidized waste material 58. Hot air 82 may be supplied in the bioreactor 80 prior to supplying any microorganisms 44. The hot air 82 would serve to destroy any remaining oxidizing agent that is present in the bioreactor 80 prior to the microorganisms 44 consuming the oxidized organic material 58. Additional oxidizing agent 74 can also be added after the initial supply as can additional microorganisms 44. However, it should also be understood that the bioreactor 80 is not limited to a vessel and can include any location, including a landfill mass 70, in which the oxidized waste material 58 is consumed by microorganisms 44.

Again, in certain embodiments, a temperature sensor 78 may be placed in the bioreactor 80 to detect such rapid changes in temperature. If needed, various methods may be utilized to slow growth of the microorganisms 44 and decrease the temperature of the oxidized waste material 58. One such method that may be utilized with aerobic microorganisms 44 involves adding a gas into the bioreactor 80 which will create anaerobic conditions. Gases such as carbon dioxide or nitrogen would be suitable to create anaerobic conditions.

In certain embodiments the temperature sensor 78 may trigger anaerobic conditions to slow the growth of the microorganisms 44.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process for reducing solid waste volume comprising:
    loading organic material into a vessel, said vessel having at least a first zone and a second zone;
    supplying an oxidizing agent into said first zone of said vessel in the presence of an aqueous medium, wherein said oxidizing agent comprises ozone or hydrogen peroxide, said oxidizing agent oxidizing and breaking down at least a portion of said organic material;
    agitating by peristaltic action said organic material, said oxidizing agent, and said aqueous medium in said vessel to further oxidize and break down said organic material; and
    supplying a microorganism into said second zone of said vessel.

2. A process as defined in claim 1, wherein said organic material, said oxidizing agent, and said aqueous medium are agitated resulting in mixing and movement of said organic material through said vessel.

3. A process as defined in claim 1, further comprising the step of removing the processed organic material from said vessel, placing said processed organic material in a bioreactor, said microorganism consuming the oxidized organic material resulting in a reduction of said solid waste volume.

4. A process as defined in claim 1, further comprising the step of supplying hot air in said bioreactor and thereafter supplying additional microorganism into said bioreactor, said hot air destroying any remaining oxidizing agent, said additional microorganism consuming the oxidized organic material resulting in a reduction of said solid waste volume.

5. A process as defined in claim 1, wherein a hot air curtain is located in said vessel to prevent backflow of said oxidizing agent.

6. A process as defined in claim 1, further comprising the step of supplying hot air in said vessel prior to supplying said microorganism, said hot air destroying any remaining oxidizing agent in said vessel prior to said microorganism consuming said oxidized organic material.

7. A process as defined in claim 1, wherein said organic material, said oxidizing agent, and said aqueous medium are agitated with an auger, said auger rotating within said vessel causing reduction in the size of said organic material, said rotation of said auger resulting in movement of said organic material through said vessel.

8. A process as defined in claim 1, wherein said vessel is located on a vehicle.

9. A process as defined in claim 1, wherein said organic material is reduced in size prior to being loaded in said vessel.

10. A process as defined in claim 1, wherein no oxidizing agent is found within said second zone of said vessel.

* * * * *